United States Patent
Visser

(10) Patent No.: US 10,716,719 B2
(45) Date of Patent: Jul. 21, 2020

(54) DIAPER FASTENER

(71) Applicant: Snappi Holdings (Pty) Ltd, Waltloo (ZA)

(72) Inventor: Hendrik Schalk Visser, Hermanus (ZA)

(73) Assignee: SNAPPI HOLDINGS (PTY) LTD, Waltloo (ZA)

( * ) Notice: Subject to any disclaimer, the term of this patent is extended or adjusted under 35 U.S.C. 154(b) by 403 days.

(21) Appl. No.: 15/643,854

(22) Filed: Jul. 7, 2017

(65) Prior Publication Data

US 2018/0008490 A1 Jan. 11, 2018

(30) Foreign Application Priority Data

Jul. 11, 2016 (GB) .................................. 1612036.2

(51) Int. Cl.
*A61F 13/56* (2006.01)
*A61F 13/62* (2006.01)

(52) U.S. Cl.
CPC ........ *A61F 13/5622* (2013.01); *A61F 13/622* (2013.01)

(58) Field of Classification Search
CPC ................ A61F 13/5622; A61F 13/622; A61F 13/5633; A41F 1/00; Y10T 24/31; Y10T 24/316

See application file for complete search history.

(56) References Cited

U.S. PATENT DOCUMENTS

| 2,114,561 A | * | 4/1938 | Hausmann | ............... A41F 11/00 |
| | | | | 2/309 |
| 2,919,946 A | * | 1/1960 | Miener | ................... E05C 17/36 |
| | | | | 292/288 |
| 4,962,571 A | * | 10/1990 | Visser | ....................... A41F 1/00 |
| | | | | 24/265 H |
| D320,575 S | * | 10/1991 | Crafford | ...................... D11/200 |
| D321,673 S | * | 11/1991 | Crafford | ...................... D11/200 |
| 5,077,868 A | | 1/1992 | Visser | |

(Continued)

FOREIGN PATENT DOCUMENTS

| CN | 2379117 | 5/2000 |
| EP | 0 288 285 | 10/1988 |
| ZA | 2009/07687 | 6/2010 |

*Primary Examiner* — Robert Sandy
*Assistant Examiner* — Louis A Mercado
(74) *Attorney, Agent, or Firm* — Womble Bond Dickinson (US) LLP

(57) ABSTRACT

A diaper fastener is provided of the type having a substantially planar elastically extensible base member and three spaced hook units that have teeth operable to engage the fabric of a diaper in relevant zones thereof with the elastically extensible part stretched and operative to maintain the teeth in engagement with the diaper fabric to hold the diaper in its functional position. At least one of the hook units and generally all three are each composed of two parts that are permanently clipped together from opposite sides of the base member by inter-engaging formations. One of the parts has the hook teeth formed integral therewith and the two parts co-operate with the base member to physically locate the hook unit on the base member. Preferably, each hook unit is carried by an arm forming part of the planar base. Each hook unit has a hook part and a clamping part.

9 Claims, 3 Drawing Sheets

(56) References Cited

U.S. PATENT DOCUMENTS 6,438,805 B1 * 8/2002 Goss .................... A47C 21/026
24/171
8,365,361 B1 * 2/2013 Ahern .................... A47C 21/02
24/338

* cited by examiner

DIAPER FASTENER

CROSS REFERENCE TO RELATED APPLICATIONS

This application claims the benefit of British application number 1612036.2, filed Jul. 11, 2016, which is incorporated herein by reference in its entirety and for all purposes.

FIELD OF THE INVENTION

This invention relates to a diaper fastener. More particularly, the invention relates to a diaper fastener configured to easily and safely hold together the free ends of a cloth or woven fabric diaper in use. In particular, the invention relates to a diaper fastener of the type described in our granted patent publication ZA200907687 that is incorporated herein by reference in its entirety.

BACKGROUND TO THE INVENTION

A diaper fastener that at least partially alleviates some of the difficulties associated with the use of safety pins for fastening a cloth or fabric diaper in position on an infant was disclosed by the inventor in U.S. Pat. No. 5,077,868. That product has been progressively developed over the years and the present form of the product is described in our patent publication ZA200907687. The product has a planar base member which has a central zone from which three elastically extensible arms radiate. The free ends of the arms have integrally formed pull tabs which have a generally oval shape for ease of grip between a thumb and forefinger to permit extension of the arms.

Each pull tab partially overlaps a separately molded rigid hook member which includes a number of teeth slanted so as to point in a general direction towards the central zone so that the teeth are drawn towards and engage the fabric of a diaper in relevant zones thereof by the stretched elastic zone in use. Each hook formation is attached to its associated elastic arm by means of a narrow integral stem that extends through a molded slot in the arm adjacent the pull tab and has a rather large head formation on the outside of the elastic. Assembly of the hook member onto the elastic extensible arms is achieved by passing the rather large head formation through the slot whilst stretching the material around the slot.

There is a potential that a rigid hook member could become separated from the planar base member either as a consequence of the stem fracturing or the elastic material adjacent to the slot tearing and thereby form a separate element that could cause an infant to choke or become otherwise injured thereby.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

Applicant therefore considers it to be appropriate to take measures to avoid such a situation arising.

SUMMARY OF THE INVENTION

In accordance with the invention there is provided a diaper fastener comprising a substantially planar base member, at least a part of which is elastically extensible, and three spaced hook units associated with the base member with said elastically extensible part interposed between at least two of such hook units, such hook units having teeth operable to engage the fabric of a diaper in relevant zones thereof with the elastically extensible part stretched and operative to maintain the teeth in engagement with the diaper fabric to hold the diaper in its functional position, wherein at least one of the hook units is composed of two parts that are permanently clipped together from opposite sides of the base member by inter-engaging formations and wherein at least one of the parts has the hook teeth formed integral therewith and the two parts co-operate with the base member to physically locate the hook unit on the base member.

Further features of the invention provide for the said one of the hook units to be attached to a distal end region of an elastically extensible arm that forms part of the planar base member and connects it to a central zone of the base member; and for each of the three hook units to be similarly composed of two parts clipped together in the manner defined in which instance the planar base is composed of a central zone from which three elastically extensible arms radiate each with a hook unit at or towards its distal end; for the distal end region of each arm to have a divergent shape with the hook unit being configured to prevent the arm from pulling out of the hook unit.

Additional features of the invention provide for each hook unit to comprise a hook part and a clamping part with the clamping part being channel shape in cross-section with flanges having inwardly directed clipping formations shaped to provide a predominantly one-way clipping action with corresponding formations on the edges of the hook part to provide suitable permanency of a clipped attachment thereof; for an upstanding stem to be integrally formed centrally across the width of the channel of the clamping part with the stem being sufficiently long to pass through a corresponding slot in the associated part of the planar base member and into a co-operating aperture in the hook part so as to be capable of guiding the two parts of the hook unit into co-operating positions during assembly thereof; for the co-operating regions of the hook part and clamping part to diverge in a direction away from the central zone with the hook part having shoulders for abutment by corresponding zones of the clamping part to assist in positively locating the two parts of a hook unit relative to each other to accommodate tension applied to the elastic arm; and for the distal end region of each arm to be formed into a pull tab that can be engaged between a thumb and forefinger to enable the associated arm to be elastically extended.

Still further features of the invention provide for the pull tabs to at least partially overlap the associated hook unit with the pull tab being shaped so as to be easily gripped between a thumb and forefinger for facilitating extension of the arms of the base member; and for each pull tab to be generally solid and include an outer rim which is partly free of the rest of the tab so that it can be separately pulled over the hook part so that the teeth of the hook unit are shielded at least to some extent; for the outer rim of the tab to have at least one raised formation thereon that increases the maximum cross-sectional thickness of the rim.

The above and other features of the invention will be more fully understood from the following description of one embodiment thereof with reference to the accompanying drawings.

DETAILED DESCRIPTION WITH REFERENCE TO THE DRAWINGS

Figure 1:
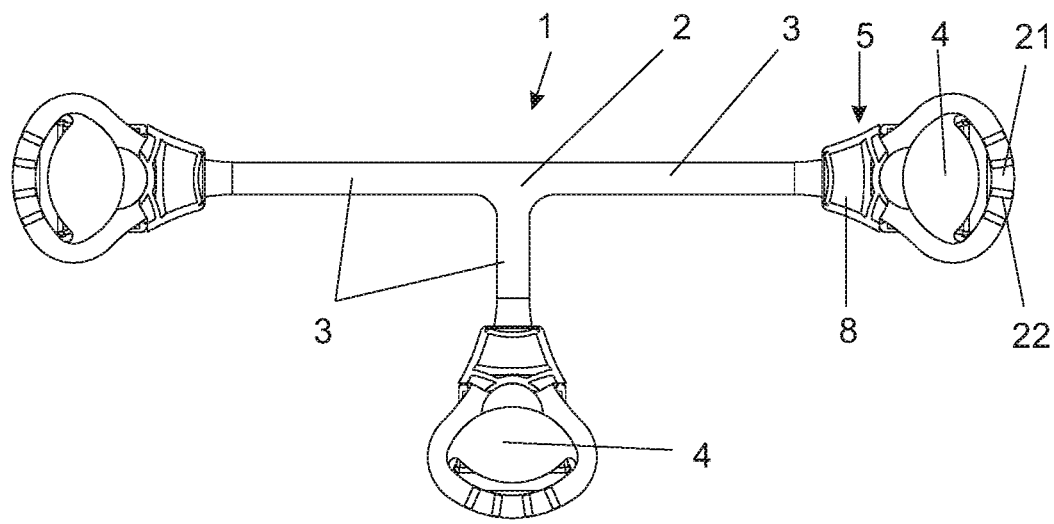
FIG. 1 is a top plan view of a diaper fastener according to the invention.
Figure 2:
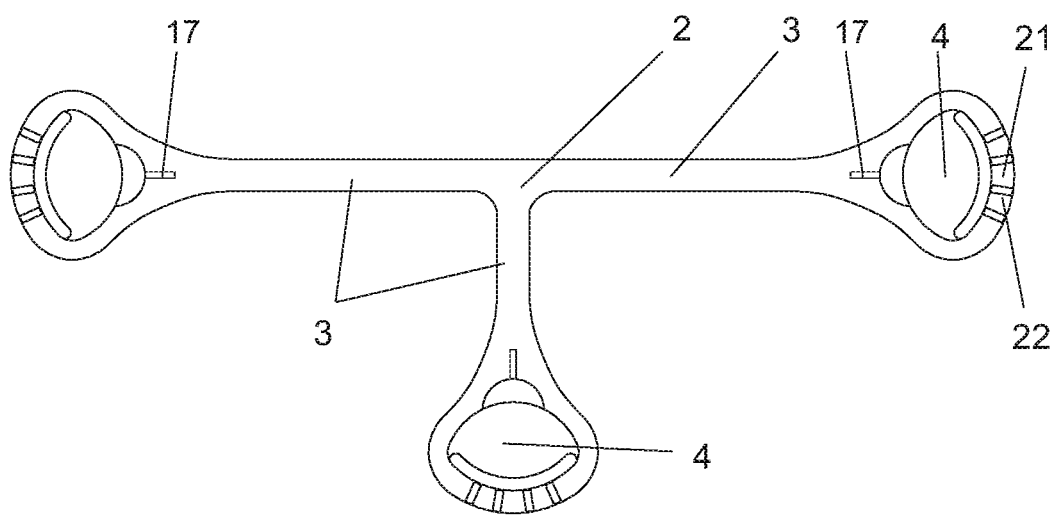
FIG. 2 is the same as FIG. 1 with the hook units removed.
Figure 3:
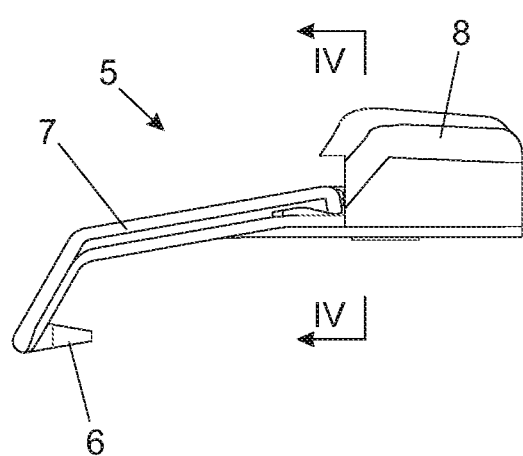
FIG. 3 is side view of an assembled hook unit with the planar base member absent.
Figure 4:
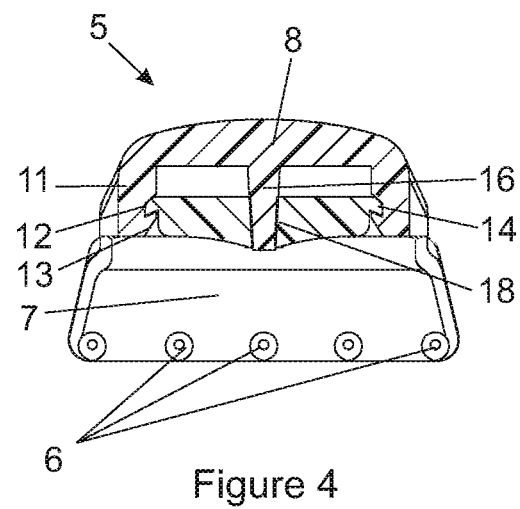
FIG. 4 is a cross section taken along line IV to IV in FIG. 3.
Figure 5:
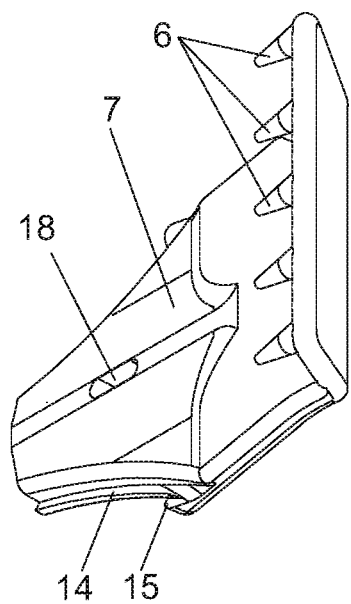
FIG. 5 is a three-dimensional view showing the underneath of the hook part and co-operating formations for engagement by the clamping part of each hook unit.
Figure 6:
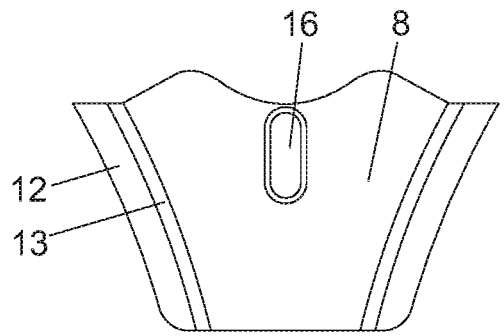
FIG. 6 is an underneath view of the clamping part of the hook unit.
Figure 7:
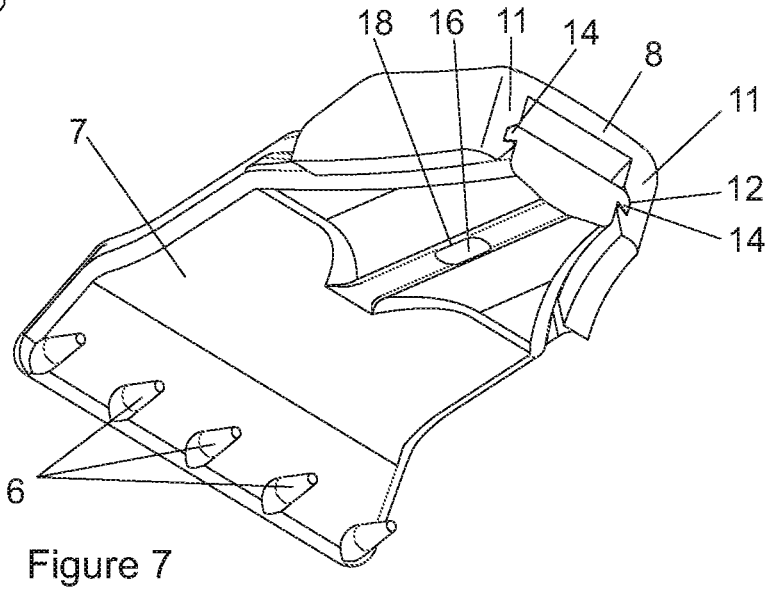
FIG. 7 is a rear three-dimensional view showing primarily the hook part of the hook unit engaged by a clamping part and illustrating the entrance for the elastic arm.
Figure 8:
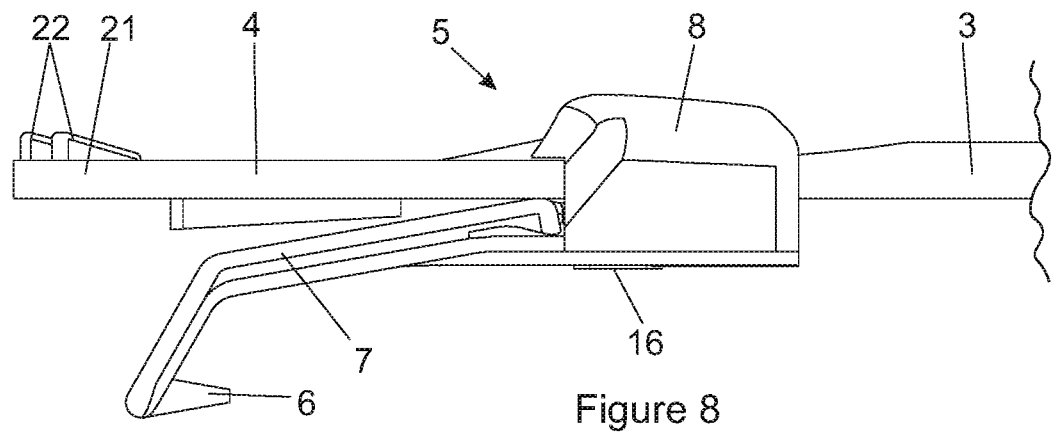
FIG. 8 is a side view of an assembled hook unit in situ on an end of an elastic arm.
Figure 9:
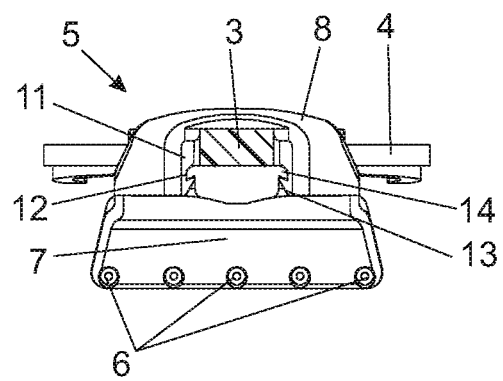
FIG. 9 is an end view thereof taken in a direction towards the teeth.
Figure 10:
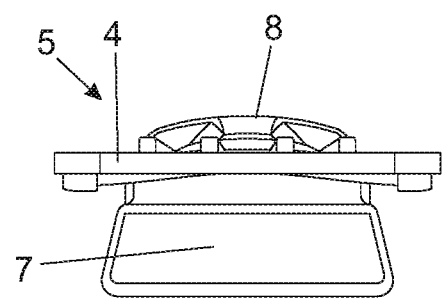
FIG. 10 is an end view thereof in the opposite direction.
Figure 11:
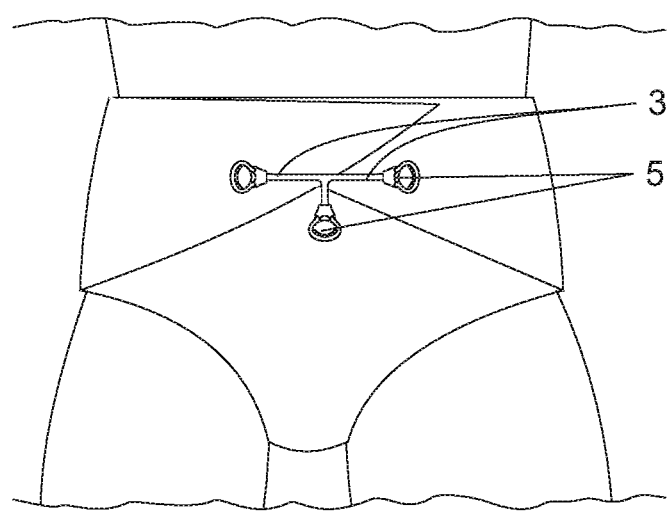
FIG. 11 is a schematic illustration of a diaper fastener of the type with which this invention is concerned in an operative position.

The accompanying drawings show an embodiment of diaper fastener that includes a one piece elastic planar base member (1) which has a central zone (2) from which three elastically extensible arms (3) radiate basically in the shape of a squat Tee. The free ends of the arms have integrally formed pull tabs (4) which have a generally oval shape for ease of grip between a thumb and forefinger to permit extension of the arms and a hook unit (5) attached thereto and the oval shape merges with the arm by way of a smoothly curved outer edge, as shown clearly in FIG. 2.

The hook units have teeth (6) operable to engage the fabric of a diaper in relevant zones thereof with the elastically extensible part stretched and operative to maintain the teeth in engagement with the diaper fabric to hold the diaper in its functional position.

As provided by this invention, each hook unit is composed of two parts that are permanently clipped together from opposite sides of the arm of the base member by inter-engaging formations, in this embodiment of the invention a hook part (7) and a clamping part (8). The hook part (7) has the hook teeth (6) formed integral therewith and the two parts co-operate with the arm of the base member to physically locate the hook unit on the arm.

The clamping part (8) is of channel shape in cross-section with flanges (11) having inwardly directed longitudinally extending clipping formations in the form of grooves (12) shaped in the manner of a saw tooth shape of groove having a sloped entrance surface (13) to provide a predominantly one-way clipping action. Corresponding formations in the form of ridges (14) are provided along the edges of the hook part as will become more apparent from the following. The co-operating formations of the hook part and clamping part diverge in a direction away from the central zone and the hook part has shoulders (15) for abutment by corresponding zones of the clamping part to assist in positively locating the two parts of a hook unit relative to each other and so as to accommodate and retain the arm when tension is applied to the elastic arm.

An upstanding stem (16) is formed integral with the web portion of the channel of the clamping part centrally across its width. The stem extends at right angles to the arm and is sufficiently long to pass through a corresponding slot (17) through the arm (see FIG. 2) of the associated planar base member and into a co-operating aperture (18) in the hook part so as to be capable of guiding the two parts of the hook unit into co-operating positions during assembly thereof. The arrangement is such that the stem may be threaded through the slot in the arm and located in the entrance to the co-operating aperture (18) preparatory to forcing the two parts of the hook unit together so that the ridges engage in the grooves in substantially irreversible manner. In so doing the ridges engage the sloped entrance surface and force the flanges apart to allow the hook part to enter between the flanges that snap back into their normal positions when the ridges align with the grooves in the flanges. At the same time the upstanding stem enters further into the aperture in the hook part. In the fully installed position, the free end of the upstanding stem is slightly proud of the opposite outer surface of the hook part.

The upstanding stem is conveniently a flat stem orientated in a plane extending in the direction of the arm and the co-operating aperture is dimensioned to closely receive the free end of the upstanding stem and to receive it in sliding relationship as the two parts of the hook unit are moved towards each other to effect a clipping of the parts together.

The shoulders (15) formed at the ends of the ridges (14) on the hook part that are furthest apart and thus furthest from the central zone effectively prevent the clamping part from separating from the hook part in a plane parallel to that of the arm of the planar base. The whole arrangement provides suitable permanency and security of the clipped attachment of the two parts of a hook unit together.

As described in our earlier granted patent number 2009/07687 the distal end region of each arm is formed into a pull tab (4) that can be engaged between a thumb and forefinger to enable the associated arm to be elastically extended. The pull tabs at least partially overlap the associated hook unit with the pull tab being shaped so as to be easily gripped between a thumb and forefinger for facilitating extension of the arms of the base member.

Each pull tab is generally solid or continuous and includes an outer rim (21) which is partly separated from the rest of the tab so that it can be pulled over the hook part to shield the teeth of the hook unit \ at least to some extent. The outer rim of the tab preferably has at least one, and preferably a series of evenly spaced enlarged zones (22) thereon that increases the maximum cross-sectional thickness of the rim. The ridges of the series extend across the outer rim generally at right angles to an outer edge of the rim and are shaped to fit between the teeth of the hook unit when in the shielding position so as to prevent the outer rim from moving out of position easily. This arrangement can be more fully understood from the description in our said earlier patent.

It will be appreciated that the invention is not limited to the embodiment described above and many variations may be made without departing from the scope of the invention defined herein.

Throughout the specification unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A diaper fastener comprising a substantially planar base member, wherein at least part of the base member is elastically extensible, and three spaced hook units associated with the base member with the elastically extensible part of the base member interposed between at least two of the hook units, the hook units having teeth operable to engage a fabric of a diaper in relevant zones thereof with the elastically extensible part of the base member stretched and operative to maintain the teeth in engagement with the fabric to hold the diaper in its functional position, wherein each of the hook units is composed of two parts that are permanently clipped together from opposite sides of the base member by inter-engaging formations of the two parts, wherein one of the two parts has the teeth formed integral therewith, and wherein the two parts co-operate with the base member to physically locate the hook unit on the base member.

2. The diaper fastener as claimed in claim 1 in which the planar base member is composed of a central zone from which three elastically extensible arms radiate, each elastically extensible arm having one of the hook units attached to a distal end region of the elastically extensible arm.

3. The diaper fastener as claimed in claim 2 in which the distal end region of each elastically extensible arm has a divergent shape with the hook unit being configured to prevent the elastically extensible arm from pulling out of the hook unit.

4. The diaper fastener as claimed in claim 1 in which each of the hook units comprises a hook part and a clamping part with the clamping part being channel shape in cross-section with flanges having inwardly directed clipping formations shaped to provide a predominantly one-way clipping action with corresponding formations on edges of the hook part to provide substantial permanency of a clipped attachment thereof.

5. The diaper fastener as claimed in claim 4 in which an upstanding stem is integrally formed centrally across a width of the channel of the clamping part with the stem being sufficiently long to pass through a corresponding slot in an associated part of the planar base member and into a co-operating aperture in the hook part so as to be capable of guiding the two parts of the hook unit into co-operating positions during assembly thereof.

6. The diaper fastener as claimed in claim 4 in which co-operating regions of the hook part and the clamping part diverge in a direction away from a central zone of the planar base member, with the hook part having shoulders for abutment by corresponding zones of the clamping part to assist in positively locating the two parts of the hook unit relative to each other to accommodate tension applied to the elastically extensible part of the base member.

7. The diaper fastener as claimed in claim 4 in which the base member in a region of each of the hook units is formed into a pull tab that can be engaged between a thumb and forefinger to enable the elastically extensible part to be elastically extended.

8. The diaper fastener as claimed in claim 7 in which the pull tabs at least partially overlap the associated hook unit with the pull tab being shaped so as to be gripped between the thumb and forefinger for facilitating extension of the elastically extensible part of the base member and wherein each of the pull tabs is generally solid and includes an outer rim which is partly free of a rest of the pull tab so that it can be separately pulled over the hook part so that the teeth of the hook unit are shielded by the outer rim.

9. The diaper fastener as claimed in claim 8 in which the outer rim of each of the pull tabs has at least one raised formation thereon that increases a maximum cross-sectional thickness of the outer rim.

\* \* \* \* \*